United States Patent
Lin

(10) Patent No.: US 8,790,695 B2
(45) Date of Patent: Jul. 29, 2014

(54) MEDICINAL CARRIERS, AND PREPARATION METHOD AND USES THEREOF

(71) Applicant: China Medical University, Taichung (TW)

(72) Inventor: Yu-Hsin Lin, Taichung (TW)

(73) Assignee: China Medical University, Taichung (TW)

( * ) Notice: Subject to any disclaimer, the term of this patent is extended or adjusted under 35 U.S.C. 154(b) by 0 days.

(21) Appl. No.: 13/686,363

(22) Filed: Nov. 27, 2012

(65) Prior Publication Data

US 2014/0099371 A1    Apr. 10, 2014

(30) Foreign Application Priority Data

Oct. 5, 2012 (TW) .............................. 101136910 A

(51) Int. Cl.

| | |
|---|---|
| A61K 9/36 | (2006.01) |
| A61K 9/14 | (2006.01) |
| A61K 8/73 | (2006.01) |
| A01K 43/04 | (2006.01) |
| A61K 31/545 | (2006.01) |
| A01N 25/00 | (2006.01) |
| C08B 37/08 | (2006.01) |
| A61K 39/02 | (2006.01) |

(52) U.S. Cl.
CPC ...................................... *A61K 9/146* (2013.01)
USPC ..... 424/480; 424/488; 424/70.13; 424/234.1; 514/54; 514/197; 514/781; 536/20

(58) Field of Classification Search
None
See application file for complete search history.

(56) References Cited

FOREIGN PATENT DOCUMENTS

| CN | 101856432 B | * | 1/2012 |
|---|---|---|---|
| JP | 2006500975 | | 1/2006 |
| JP | 2009511549 | | 3/2009 |
| JP | 2011178722 | | 9/2011 |
| WO | 2004012676 A2 | | 2/2004 |
| WO | 2005025538 A1 | | 3/2005 |
| WO | WO 2006031420 A2 | * | 3/2006 |
| WO | 2007042572 A1 | | 4/2007 |
| WO | WO 2010088294 A1 | * | 8/2010 |

OTHER PUBLICATIONS

Oungbho et al. "Chitosan-Gelatin sponge as drug carrier system", European Journal of Pharmaceutical Sciences, vol. 4, supplemental 1, Sep. 1996, pp. 155.*
Kratz et al. "Heparin-chitosan complexes stimulate wound healing in human skin", Scand J Plast Reconstr Surg. Jun. 1997, 31(2):119-23.*
Machine translation of CN 101856432A.*

(Continued)

*Primary Examiner* — Ernst V Arnold
*Assistant Examiner* — Kyung Sook Chang
(74) *Attorney, Agent, or Firm* — Ping Wang; Andrews Kurth LLP

(57) ABSTRACT

A medicinal carrier is provided. The medicinal carrier comprises a first component, which is a biocompatible polymer with an amino group (—$NH_2$); a saccharide; and a second component which is a biocompatible material. The saccharide grafts to the first component via the amino group (—$NH_2$) of the first component, and the first component bonds to the second component via an ionic bond. The medicinal carrier can protect the medicine from gastric acid and swell or decompose to release the medicine under a specific pH condition, thus, showing a good applicability.

19 Claims, 4 Drawing Sheets
(2 of 4 Drawing Sheet(s) Filed in Color)

Health mice          *Helicobacter pylori* infected mice

Deionized water    nanocarrier without active agent (control group)    amoxicillin    nanocarrier encapsulating amoxicillin

(56) References Cited

OTHER PUBLICATIONS

Aristippos Gennadios et al., "Protein-based films and coatings" (2007, CRC press, p. 285 and 298).*

Zih-Sian He, "Application of Genipin Crosslinking of Targeting Nanoparticles for Inhibited Helicobacter pylori: in vitro and in vivo studies", Jul. 6, 2012 (Abstract).

Obara, K. et al., "Controlled release of paclitaxel from photocrosslinked chitosan hydrogels and its subsequent effect on subcutaneous tumor growth in mice", J Controlled Release, Dec. 10, 2005;110(1):79-89.

Lin, Y. H. et al., "Development of pH-responsive chitosan/heparin nanoparticles for stomach-specific anti-Helicobacter pylori therapy", Biomaterials, vol. 30, 2009, pp. 3332-3342.

Ramteke, Suman et al., "Amoxicillin, clarithromycin, and omeprazole based targeted nanoparticles for the treatment of H. pylori", Journal of Drug Targeting, vol. 17, No. 3, 2009, pp. 225-234.

* cited by examiner

MEDICINAL CARRIERS, AND PREPARATION METHOD AND USES THEREOF

CROSS-REFERENCES TO RELATED APPLICATIONS

This application claims the benefit of Taiwan Patent Application No. 101136910, filed on Oct. 5, 2012, in the Taiwan Intellectual Property Office, the disclosure of which is incorporated herein in its entirety by reference.

BACKGROUND OF THE INVENTION

1. Field of the Invention

The present invention relates to a medicinal carrier, its preparation method and uses, and especially relates to a medicinal carrier for anti-*Helicobacter pylori*, its preparation method and uses.

2. Descriptions of the Related Art

*Helicobacter pylori* is a Gram-negative bacterium mainly found in the stomach and duodenum of the organism. *Helicobacter pylori* will form a cloudy film on the surface of the gastric wall when adhering to the surface of the gastric mucosa layer, and produce urease to hydrolyze the urea in the stomach to produce $NH_3$ and $CO_2$, thereby neutralizing and increasing the pH value in the stomach to pH 4.5 to pH 7.4. Such a pH value is suitable for the colonization of *Helicobacter pylori* in the stomach of the organism.

According to statistics, over 50% of the populations in the world are infected with *Helicobacter pylori* in the digestive system. Some *Helicobacter pylori*-infected populations suffer from symptoms, such as chronic inflammation of the gastric mucosa, peptic ulcer, and gastric cancer. Peptic ulcers mainly occur in the stomach pylorus or the duodenum of the small intestine, while patients of peptic ulcers are usually diagnosed as patients of gastric ulcer. Common symptoms of gastric ulcer are abdominal pain, loss of appetite, weight loss, etc.

Antibiotics, such as amoxicillin, clarithromycin, tetracycline, and metronidazole, are usually used in clinic to treat the diseases caused by the infection of *Helicobacter pylori*. However, because antibiotics are often destroyed by gastric acid or cannot pass through the gastric mucosa to the colonization site of *Helicobacter pylori*, antibiotic treatment has not been able to achieve a good therapeutic efficacy. In addition, patients treated with antibiotics frequently may suffer from side effects of dizziness, abdominal pain, diarrhea, allergies, etc.

In view of the above, there is still a need for a medicine that can more effectively cure diseases associated with the infection of *Helicobacter pylori*. The present invention is a research for the above demand, and provides a medicinal carrier which can target *Helicobacter pylori* and swell or decompose under a specific pH condition. Therefore, the medicinal carrier can be used to encapsulate a medicine for anti-*Helicobacter pylori*, and thereby, assists the medicine to reach the colonization site of *Helicobacter pylori* to achieve anti-*Helicobacter pylori* efficacy.

SUMMARY OF THE INVENTION

One objective of this invention is to provide a medicinal carrier, comprising: a first component, which is a biocompatible polymer with an amino group ($-NH_2$); a saccharide, which is selected from the group consisting of glucose, fucose, galactosamine, mannose, and combinations thereof; and a second component, which is a biocompatible material; wherein the saccharide grafts to the first component via the amino group ($-NH_2$) of the first component and the first component bonds to the second component via ionic bond.

Another objective of this invention is to provide a use of the aforesaid medicinal carrier in the manufacture of a medicament for anti-*Helicobacter pylori*.

Yet a further objective of this invention is to provide a method for preparing a medicinal carrier, comprising:

(a) providing a saccharide-grafted first component, wherein the first component is a biocompatible polymer with an amino group ($-NH_2$), and the saccharide is selected from the group consisting of glucose, fucose, galactosamine, mannose, and combinations thereof;

(b) dissolving the saccharide-grafted first component into water to provide a first solution;

(c) dissolving a second component into water to provide a second solution, wherein the second component is a biocompatible material;

(d) optionally, providing a third solution comprising a third component selected from the group consisting of an active agent, a protective agent, a crosslinking agent, and combinations thereof; and (e) mixing the first solution, the second solution, and the optional third solution to form the medicinal carrier.

Yet a further objective of this invention is to provide a method for treating or alleviating a disease or condition associated with *Helicobacter pylori*, comprising administrating to a subject in need an effective amount of the aforesaid medicinal carrier.

The detailed technology and preferred embodiments implemented for the present invention are described in the following paragraphs accompanying the appended drawings for people skilled in this field to well appreciate the features of the claimed invention.

BRIEF DESCRIPTION OF THE DRAWINGS

The patent application contains at least one drawing executed in color. Copies of this patent document with color drawing(s) will be provided by the Office upon request and payment of the necessary fee.

DESCRIPTION OF THE PREFERRED EMBODIMENT

Figure 1:
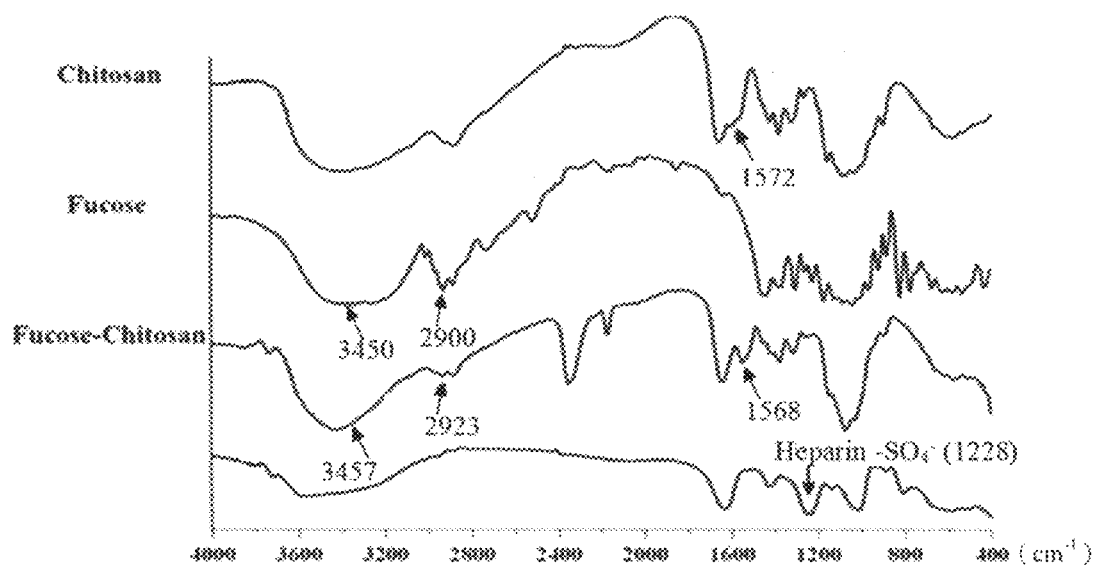
FIG. 1 is a Fourier transform infrared spectrum of a fucose-grafted chitosan.

The following will describe some embodiments of the present invention in detail. However, without departing from the spirit of the present invention, the present invention may be embodied in various embodiments and should not be limited to the embodiments described in the specification. In addition, unless otherwise stated herein, the terms "a (an)", "the", or the like used in this specification (especially in the claims hereinafter) shall be understood to encompass both the singular and plural forms.

As described above, when the antibiotics are used clinically to treat *Helicobacter pylori*-infected patients, the antibiotics are often destroyed by gastric acid and cannot maintain their therapeutic efficacy, or the antibiotics cannot successfully eradicate *Helicobacter pylori* due to the difficulty of passing through the gastric mucosa, and thus, the antibiotics cannot achieve a good therapeutic efficacy. The present invention overcomes the disadvantages of traditional therapies, and provides a medicinal carrier that can target *Helicobacter pylori*, which can pass through the barrier of gastric mucosal layer, protect the anti-*Helicobacter pylori* medicine from the gastric acid, thereby increasing the availability of the medicine, and have a good biocompatibility.

Therefore, the present invention provides a medicinal carrier, comprising a first component, which is a biocompatible polymer with an amino group (—NH$_2$); a saccharide, which is selected from the group consisting of glucose, fucose, galactosamine, mannose, and combinations thereof; and a second component, which is a biocompatible material. The saccharide grafts to the first component via the amino group (—NH$_2$) of the first component, and the first component bonds to the second component via an ionic bond.

In the medicinal carrier of the present invention, the first component can be any suitable biocompatible polymer with an amino group (—NH$_2$). For example, but not limited to, the first component may be selected from the group consisting of chitosan, collagen, gelatin, ethylene glycol-chitosan, poly (ethylene glycol)-chitosan, and combinations thereof. Preferably, the first component is selected from the group consisting of chitosan, gelatin, and combinations thereof.

The saccharide suitable for the present invention may be any saccharide which can bind with the surface of *Helicobacter pylori*. For example, but not limited to, the medicinal carrier of the present invention may comprise a saccharide selected from the group consisting of glucose, fucose, galactosamine, mannose, and combinations thereof. Preferably, the medicinal carrier of the present invention comprises fucose.

Without being limited by theories, it is believed that in the medicinal carrier of the present invention, the saccharide could graft to the first component via its hydroxyl group (—OH) and the amino group (—NH$_2$) of the first component. In general, the saccharide in the medicinal carrier of the present invention is in an amount that can make about 5% to about 30% of the total amino group (—NH$_2$) of the first component to graft with the saccharide, and preferably about 10% to about 15%. In addition, in the case that the medicinal carrier of the present invention comprises a plurality of materials as the first component (e.g., using two materials as the first component, gelatin and chitosan), depending on the practical demand and manufacturing convenience, the adopted saccharide may graft to each material, or merely graft to one of the materials, as long as the purpose of targeting *Helicobacter pylori* can be achieved.

The medicinal carrier of the present invention also comprises a second component, which may be any biocompatible material that can bond to the first component via an ionic bond. For example, but not limited to, the second component may be a substance with a pharmaceutical activity, such as anti-*Helicobacter pylori*. For example, the second component may be a tea polyphenol, such as catechin which comprises epicatechin (EC), epigallocatechin (EGC), epicatechin gallate (ECG), and epigallocatechin gallate (EGCG) as the main components, wherein EGCG makes the highest percentage of catechin. The second component could also be a biocompatible material without pharmaceutical activity, and for example, may be selected from the group consisting of heparin, poly(glutamic acid), tripolyphosphoric acid, poly (acrylic acid), phospholipid, sodium alginate, and combinations thereof. In some embodiments of the present invention, the second component of the medicinal carrier is selected from the group consisting of heparin, poly(glutamic acid), sodium alginate, catechin, and combinations thereof.

Without being limited by theories, it is believed that in the medicinal carrier of the present invention, the first component is dissociated as a substance with positive charge in the preparation solution during the preparation process of the carrier, and the second component is dissociated as a substance with negative charge. The first component and the second component attract each other by the ionic interaction between the positive ions and negative ions, and bonds to each other via an ionic bond to provide the medicinal carrier of the present invention. In general, in the medicinal carrier of the present invention, the first component and the second component are used in a weight ratio of about 1:0.1 to 1, preferably about 1:0.2 to 0.4.

The medicinal carrier of the present invention may optionally comprise a third component to increase the applicability of the medicinal carrier. For example, but not limited to, the third component may be selected from the group consisting of an active agent, a protective agent, a crosslinking agent, and combinations thereof. The active agent, for example, may be an ingredient with an activity for anti-*Helicobacter pylori*, comprising, but not limited to amoxicillin, clarithromycin, tetracycline, metronidazole, curcumin, berberine, and combinations thereof. Preferably, the active agent is at least either amoxicillin or curcumin. The protective agent may be an anti-freezing agent which can protect the structure of the medicinal carrier in the subsequent freeze-drying process, such as trehalose, glucose, lactose, glycerin, and combinations thereof. As for the crosslinking agent, it can cross-link with the first component and/or the second component in the medicinal carrier of the present invention to increase the structural stability of the medicinal carrier, and render the medicinal carrier to maintain stable at an acidic condition (e.g., pH 1.2 condition in gastric juice), while to begin to decompose to release the active agent and the active substance at a neutral condition (e.g., pH 7.4 condition in the gastric mucosa layer or in the condition of gastric epithelial cells infected by *Helicobacter pylori*). For example, but not limited thereby, the crosslinking agent useful in the medicinal carrier of the present invention may be selected from the group consisting of glutaraldehyde, genipin, epoxy resin, paraformaldehyde, formaldehyde, calcium chloride, and combinations thereof. Preferably, the medicinal carrier of the present invention comprises at least either genipin or calcium chloride as the crosslinking agent.

In the case that the third component is present, and under the premise that the desired properties of the medicinal carrier are not affected, the amount of the third component is not particularly limited, as long as it can provide the desired medical efficacy, protective effect and/or cross-linking effect. In general, if the third component, active agent, is present, the first component, the second component, and the active agent in the medicinal carrier of the present invention are used in a weight ratio of about 1:0.1 to 1:0.1 to 1, and preferably about 1:0.2 to 0.4:0.2 to 0.4. If the third component, the protective agent is present, the first component, the second component, and the protective agent are used in a weight ratio of about 1:0.1 to 1:1 to 10, and preferably about 1:0.2 to 0.4:3 to 5. If the third component, the crosslinking agent, is present, the first component, the second component, and the crosslinking agent are used in a weight ratio of about 1:0.1 to 1:0.02 to 0.2, and preferably about 1:0.2 to 0.4:0.05 to 0.1. If two or three third components are present, the amount of each component is as described above. For example, if the active agent, the protective agent, and the crosslinking agent are present, the first component, the second component, the active agent, the protective agent, and the crosslinking agent are used in a weight ratio of about 1:0.1 to 1:0.1 to 1:1 to 10:0.02 to 0.2, and preferably about 1:0.2 to 0.4:0.2 to 0.4:3 to 5:0.05 to 0.1.

The medicinal carrier of the present invention can be in a nano form, microparticle form, a hydrogel form, etc. For example, under a suitable preparation process, when gelatin is used as the first component, sodium alginate is usually used as the second component. Calcium chloride can be used as the crosslinking agent to provide a medicinal carrier in a hydrogel form. Another example is that when gelatin is used as the first component and catechin is used as the second component, a medicinal carrier in a microparticle form can be provided. Furthermore, when gelatin or chitosan is used as the first component and heparin or poly(glutamic acid) is used as the second component, a medicinal carrier in a nano form can usually be provided. It is believed that the particle size of the medicinal carrier for orally administration to the organism is preferably in nano-scale to make the medicinal carrier successfully pass through the barrier of the gastric mucosal layer to the infected site to maximize the bioavailability. Therefore, to successfully pass through the barrier of the gastric mucosal layer, the particle size of the medicinal carrier of the present invention is preferably about 100 nm to about 4 more preferably about 150 nm to about and most preferably about 200 nm to about 500 nm.

According to some embodiments of the present invention, the medicinal carrier is a fucose-grafted chitosan/heparin nanocarrier encapsulating amoxicillin, a fucose-grafted chitosan/poly(glutamic acid) nanocarrier encapsulating curcumin, or a fucose-grafted chitosan/gelatin/EGCG nanocarrier. The medicinal carrier is preferred to be a fucose-grafted chitosan/heparin nanocarrier crosslinked by genipin, encapsulating amoxicillin, and containing trehalose.

Because the medicinal carrier of the present invention comprises a saccharide which can bind to the surface of *Helicobacter pylori*, it can specifically target *Helicobacter pylori*. When the medicinal carrier of the present invention encapsulates an active agent for anti-*Helicobacter pylori* (such as amoxicillin, clarithromycin, and curcumin) or comprises an active substance for anti-*Helicobacter pylori* (such as EGCG) as the second component, it facilitates the active agent or active substance to reach the *Helicobacter pylori*-infected site. Therefore, the medicinal carrier of the present invention can be used to manufacture a medicament, especially to manufacture a medicament for anti-*Helicobacter pylori*, and the medicament can achieve the efficacy of treating or alleviating peptic ulcer, gastritis or gastric cancer.

As indicated above, because the medicinal carrier of the present invention could target *Helicobacter pylori* and encapsulate an active agent for anti-*Helicobacter pylori* or comprises an active substance for anti-*Helicobacter pylori* as the second component, the present invention also provide a method for treating or alleviating a disease or condition associated with *Helicobacter pylori*, such as treating or alleviating peptic ulcer, gastritis or gastric cancer, comprising administrating to a subject in need an effective amount of the aforesaid medicinal carrier. The type and amount of each component are as described above.

The present invention also provides a method for preparing the aforesaid medicinal carrier, comprising the following steps:

(a) providing a saccharide-grafted first component, wherein the first component is a biocompatible polymer with an amino group (—$NH_2$), and the saccharide is selected from the group consisting of glucose, fucose, galactosamine, mannose, and combinations thereof;

(b) dissolving the saccharide-grafted first component into water to provide a first solution;

(c) dissolving a second component into water to provide a second solution, wherein the second component is a biocompatible material;

(d) optionally, providing a third solution comprising a third component selected from the group consisting of an active agent, a protective agent, a crosslinking agent, and combinations thereof; and (e) mixing the first solution, the second solution, and the optional third solution to form the medicinal carrier; wherein the first component, the second component, the active agent, the protective agent, and the crosslinking agent are as defined above.

In step (a) of the method according to the present invention, the saccharide-grafted first component can be provided, for example, by separately dissolving the saccharide and the first component into the same or different solvents, and then mixing the two solutions to allow the saccharide to react with the first component, thereby grafting the saccharide to the first component. Herein, without being limited by theories, it is believed that the —OH of the saccharide could react with the —$NH_2$ of the first component to achieve grafting. The solvent useful for dissolving the saccharide and first component comprises components, such as water, acetic acid or a mixture thereof. Other solvents, such as methanol, ethanol, or a mixture thereof can further be added thereto (usually added to the solution of the first component), to promote the grafting process.

In one embodiment of the present invention, step (a) comprises mixing the fucose (as the saccharide) aqueous solution and the chitosan (as the first component) solution (acetic acid/methanol=1/1), and stirring the mixture at the presence of a reducing agent and at room temperature in the dark for about 5 to 8 hours. Then, the solvents and un-reacted materials could be removed by freeze-drying to obtain a fucose-grafted chitosan. The reducing agent useful in the present invention comprises, but is not limited to, sodium cyanoborohydride (NaCN$BH_3$), 1-ethyl-3-(3-dimethylaminopropyl) carbodiimide (EDC), etc. When performing the grafting process, depending on the desired grafting level and manufacturing convenience, the conditions (such as the concentrations of the saccharide solution and the chitosan solution, the stirring speed, and the reaction time) could be adjusted.

Afterwards, in step (b), the saccharide-grafted first component is dissolved into water to provide a first solution. Furthermore, in step (c), a second component is dissolved into water to provide a second solution. And, in an optional step (d), a third solution comprising a third component selected from the group consisting of an active agent, a protective agent, a crosslinking agent, and combinations thereof, is provided. The solvent used in the third solution is not particularly limited, as long as it has no adverse effects on the medicinal carrier of the present invention and can dissolve the third component. For example, the solvent used in the third solution may be selected from polar solvents such as water, acetic acid, methanol, ethanol, dimethyl sulfoxide, polyvinylalcohol.

After providing the first solution, the second solution, and the optional third solution, the first solution, the second solution, and the optional third solution are mixed in step (e) to form the medicinal carrier of the present invention. If the third solution is present, the first solution, the second solution, and the third solution could be mixed in any suitable order. For example, the first solution and the second solution are mixed firstly and then mixed with the third solution. Alternatively, the first solution and the third solution are mixed firstly, and then mixed with the second solution. The first solution, second solution, and third solution are mixed simultaneously.

In the method of the present invention, the properties of the obtained medicinal carrier could be controlled and adjusted by selecting the used first component and second component (and the optional third component) and the mixing condition (such as the mixing order, mixing time, and stirring speed). In general, the first component and the second component are used in a weight ratio of about 1:0.1 to 1, and preferably about 1:0.2 to 0.4. If the third component, the active agent, is present, the first component, the second component, and the active agent in the method of the present invention are used in a weight ratio of about 1:0.1 to 1:0.1 to 1, and preferably about 1:0.2 to 0.4:0.2 to 0.4. If the third component, the protective agent, is present, the first component, the second component, and the protective agent are used in a weight ratio of about 1:0.1 to 1:1 to 10, and preferably about 1:0.2 to 0.4:3 to 5. If the third component, the crosslinking agent, is present, the first component, the second component, and the crosslinking agent are used in a weight ratio of about 1:0.1 to 1:0.02 to 0.2, and preferably about 1:0.2 to 0.4:0.05 to 0.1. If two or three third components are present, the amount of each component is as described above. For example, if the active agent, the protective agent, and the crosslinking agent are present simultaneously, the first component, the second component, the active agent, the protective agent, and the crosslinking agent are used in a weight ratio of about 1:0.1 to 1:0.1 to 1:1 to 10:0.02 to 0.2, and preferably about 1:0.2 to 0.4:0.2 to 0.4:3 to 5:0.05 to 0.1.

In one embodiment of the method of the present invention, a fucose-grafted chitosan/heparin medicinal carrier in a nano form can be prepared by the following steps:

(1) performing the grafting reaction between fucose and chitosan in the presence of $NaCNBH_3$ and at room temperature for 6 hours, and then, freeze-drying the sample to collect the fucose-grafted chitosan;

(2) dissolving the obtained fucose-grafted chitosan into water;

(3) dissolving heparin into water; and (4) mixing the chitosan solution and the heparin solution evenly, and collecting the obtained nano medicinal carrier.

For the preparation of a fucose-grafted chitosan/heparin medicinal carrier comprising the third component, the third component(s) such as amoxicillin (as an active agent), trehalose (as an anti-freezing agent), and/or genipin (as a crosslinking agent) are dissolved into water, and the solution is mixed with the nanocarrier obtained from the aforesaid preparation process and stirred at room temperature for 120 minutes. Then, the sample is freeze-dried to collect the formed nano medicinal carrier. In this process, if amoxicillin, trehalose and genipin are simultaneously added as the third component, a fucose-grafted chitosan/heparin nanocarrier crosslinked by genipin, encapsulating amoxicillin, and containing trehalose could be obtained.

In another embodiment of the method according to the present invention, a fucose-grafted gelatin/sodium alginate medicinal carrier in a hydrogel form can be prepared by the following steps:

(1) performing the grafting reaction between fucose and gelatin in the presence of $NaCNBH_3$ and at room temperature for 6 hours, and then, freeze-drying the sample to collect the fucose-grafted gelatin;

(2) dissolving the obtained fucose-grafted gelatin into water;

(3) dissolving sodium alginate into water; and (4) mixing the gelatin solution and the sodium alginate solution evenly; and (5) filling the mixed solution of (4) into a syringe, and slowly dropping it into a calcium chloride solution to form a medicinal carrier in a hydrogel form. The formed medicinal carrier in a hydrogel form has a stable structure, and can be stable in an acidic condition (e.g., pH 1.2 condition in gastric juice) while beginning to decompose to release the active agent and/or the active substance at a neutral condition (e.g., pH 7.4 condition in gastric mucosa layer or in the condition of gastric epithelial cells infected by *Helicobacter pylori*). Therefore, the medicinal carrier in a hydrogel form could be used to encapsulate an active agent or the nano medicinal carrier of the present invention, to prepare a desired medicament.

In the method of the present invention, in addition to using the crosslinking agent, the stability of the obtained medicinal carrier could be increased by forming an oil/water emulsion method in step (e), and the encapsulating ratio could be increased under a condition that an active agent is encapsulated. For example, the first solution and the third solution could be mixed firstly in step (e), and then mixed with the second solution, wherein an oily solution containing a surfactant is added thereto before mixed with the second solution. Specifically, step (e) comprises the following steps: (e1) mixing the first solution and the third solution to form a first mixed solution; (e2) mixing the first mixed solution and an oily solution containing a surfactant to form a second mixed solution; and (e3) mixing the second mixed solution and the second solution to form a medicinal carrier. The surfactant may be for example, but not limited to, Tween 20, Tween 40, Tween 60, Tween 80, Span 20, Span 40, Span 60, Span 80, etc. The oil in the oily solution may be, for example, but not limited to, paraffin oil, soybean oil. In general, the surfactant and the oil are used in a volume ratio of about 0.005 to 0.02:1.

In one embodiment of the method according to the present invention, the preparation of a medicinal carrier by forming an oil/water emulsion method comprises firstly mixing a fucose-grafted chitosan solution and an amoxicillin solution with stirring evenly; adding a paraffin oil solution containing Tween 20 and stirring the mixture at a low temperature by using a homogenizer (such as 15000 to 25000 rpm) to form a homogeneous mixed solution; and then, mixing a heparin solution with the aforesaid homogeneous mixed solution evenly; and finally, obtaining a saccharide-grafted medicinal carrier encapsulating amoxicillin via centrifugation. The medicinal carrier obtained by this manner is usually in a nano form.

The present invention will be further illustrated with reference to the following examples. However, these examples are only provided for illustration purposes, but not to limit the scope of the present invention. In addition, unless otherwise stated herein, the unit "%" used thereinafter refers to "weight/volume %."

Example 1

Preparation of a Nano Medicinal Carrier Encapsulating an Active Agent (1) Preparation of a Fucose-Grafted Chitosan (Hereinafter Refers to as "Fucose-Chitosan")

Chitosan was dissolved in 50 ml solvent (1% acetic acid:methanol=1:1) to provide a 1% chitosan solution, and 0.5 g glucose was dissolved in 10 ml deionized water. The fucose solution and the chitosan solution were mixed, 0.1 g $NaCNBH_3$ was added thereto, and the mixture was magnetically stirred at room temperature in the dark for 6 hours. The reaction solution was subjected to dialysis for 3 days to remove un-reacted $NaCNBH_3$. Then, the sample was freeze-dried to obtain fucose-chitosan.

The obtained fucose-chitosan was analyzed by a Fourier transform infrared spectroscopy, and the result is shown in FIG. 1. Chitosan shows a $NH_3^+$ functional group signal at 1572 $cm^{-1}$; fucose shows CH and OH functional groups signals at 2900 $cm^{-1}$ to 3450 $cm^{-1}$; and the fucose-chitosan shows both a $NH_3^+$ functional groups signal (1568 $cm^{-1}$) and CH and OH functional groups signals (2923 $cm^{-1}$ to 3457 $cm^{-1}$). It shows that fucose successfully grafted to chitosan.

(2) Preparation of a Fucose-Chitosan/Heparin Nano Medicinal Carrier

The fucose-chitosan obtained from (1) was dissolved into water to prepare a 0.12% fucose-chitosan solution (10 ml), and a 0.1% heparin water solution (2 ml) was added thereto and stirred at room temperature for 10 minutes. Then, the sample was centrifuged to collect the precipitated fucose-chitosan/heparin nano medicinal carrier. The obtained fucose-chitosan/heparin nano medicinal carrier was dissolved in 0.5 ml deionized water for the following experiments.

Figure 2:
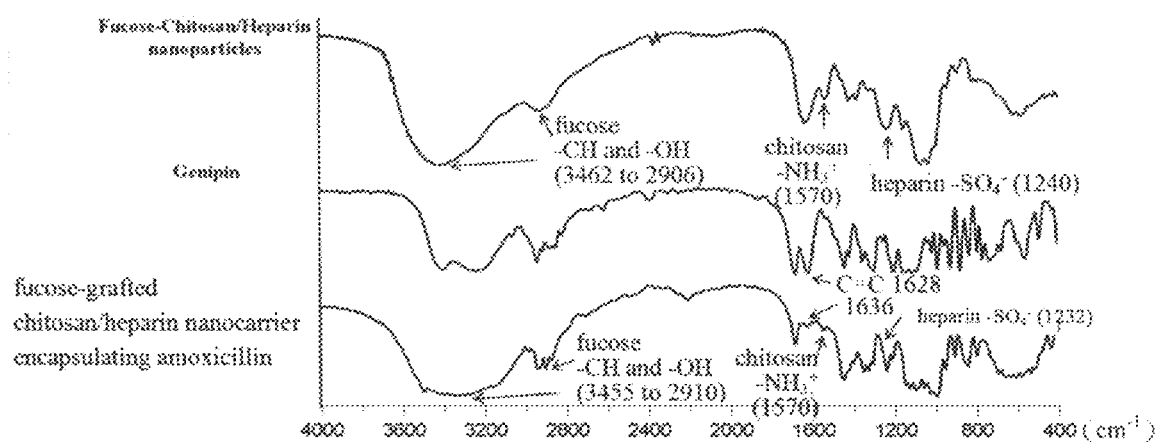
FIG. 2 is a Fourier transform infrared spectrum of a fucose-chitosan/heparin nano medicinal carrier encapsulating amoxicillin.

The obtained fucose-chitosan/heparin nano medicinal carrier was analyzed by a Fourier transform infrared spectroscopy, and the result is shown in FIG. 2. The fucose-chitosan/heparin nano medicinal carrier shows a CH functional group signal and a OH functional group signal of fucose at 3462 $cm^{-1}$ to 2906 $cm^{-1}$; shows a $NH_3^+$ functional group signal of chitosan at 1570 $cm^{-1}$; and shows a $SO_4^-$ functional group signal of heparin at 1240 $cm^{-1}$.

(3) Preparation of a Crosslinking Agent Crosslinked Fucose-Chitosan/Heparin Nano Medicinal Carrier A 12.0% trehalose (anti-freezing agent) solution (0.5 ml) and 0.075% genipin (crosslinking agent) (0.5 ml) were mixed evenly, and 0.5 ml fucose-chitosan/heparin nanocarrier solution obtained from (2) was added thereto. The sample was stirred at room temperature for 2 hours to form a fucose-chitosan/heparin nano medicinal carrier crosslinked by genipin. The crosslinked nano medicinal carrier was stored at −20° C. overnight, and collected by freeze-drying.

The obtained nano medicinal carrier was observed by a transmission electron microscopy, and its particle size is about 250 nm.

(4) Preparation of a Crosslinking Agent Crosslinked Fucose-Chitosan/Heparin Nano Medicinal Carrier Encapsulating an Active Agent A 1.6% amoxicillin solution (0.125 ml) and 24.0% trehalose (anti-freezing agent) solution (0.125 ml) were mixed evenly, and 0.25 ml 0.075% genipin (a crosslinking agent) was added to form a mixture of amoxicillin/trehalose/genipin. The fucose-chitosan/heparin nano medicinal carrier solution (0.5 ml) obtained from (1) was added thereto, and the sample was stirred at room temperature for 2 hours to form a fucose-chitosan/heparin nano medicinal carrier crosslinked by genipin and encapsulating amoxicillin.

The obtained fucose-chitosan/heparin nano medicinal carrier crosslinked by genipin and encapsulating amoxicillin was analyzed by a Fourier transform Infrared spectroscopy, and the result is shown in FIG. 2. The crosslinking agent, genipin shows a C=C functional group signal at 1628 $cm^{-1}$; and the obtained fucose-chitosan/heparin nano medicinal carrier crosslinked by genipin and encapsulating amoxicillin also has C=C functional group signal (1636 $cm^{-1}$). This result demonstrates that genipin successfully crosslinked with the fucose-chitosan/heparin nano medicinal carrier.

The obtained nano medicinal carrier was observed by a transmission electron microscopy. The result is shown in FIG. 3A, showing that the particle size of the nano medicinal carrier is about 200 nm to about 300 nm.

(5) the Medicine Encapsulating Ratio of the Obtained Nano Medicinal Carrier

The ability of the obtained nano medicinal carrier to encapsulate antibiotics (i.e., the encapsulating ratio) was determined by a high performance liquid chromatograph. Firstly, the nano medicinal carrier obtained from (4) was centrifuged at 15000 rpm, and the supernatant was collected and serial diluted. The diluted sample (50 μl) was injected into an analysis system with a mobile phase comprising 30/70% (volume/volume) acetonitrile and 0.1 M sodium dihydrogen phosphate to analyze the concentration of the amoxicillin that was not encapsulated in the nano medicinal carrier. The encapsulating ratio of the nano medicinal carrier to encapsulate the antibiotic was calculated using the following equation:

Encapsulating ratio=(the total amount of amoxicillin (weight/volume)−the amount of the non-encapsulated amoxicillin(weight/volume))/the total amount of amoxicillin(weight/volume)×100%

The result shows that the medicine encapsulating ratio of the obtained nano medicinal carrier could reach 44.8±2.3%.

Example 2

In Vitro Medicine Release Test

Figure 3:
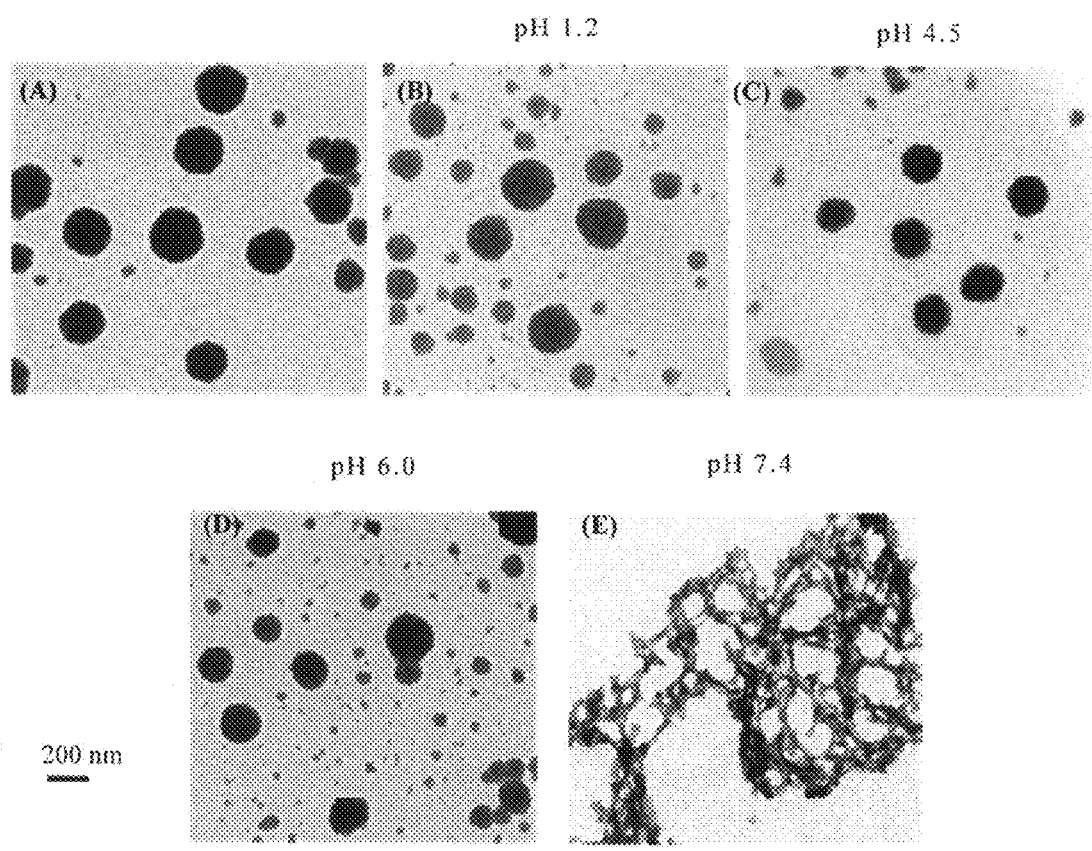
FIGS. 3A to 3E are pictures of a fucose-chitosan/heparin nano medicinal carrier crosslinked by genipin and encapsulating amoxicillin in various pH conditions.

The nano medicinal carrier obtained from example 1 (4) was placed in a pH 1.2 condition (for the simulation of gastric juice condition) or a pH 4.5, pH 6.0, or pH 7.4 condition (all for the simulation of the condition in the gastric mucosa layer or in the condition of gastric epithelial cells infected by *Helicobacter pylori*). The appearances and particle sizes of these nano medicinal carriers were observed by a transmission electron microscopy. The results are shown in FIG. 3.

As shown in FIGS. 3B to 3D, when the nano medicinal carrier was placed in the pH 1.2, pH 4.5 and pH 6.0 acidic conditions, the structure of the nano medicinal carrier was stable and non-destroyed, showing that the nano medicinal carrier can protect the encapsulated active agent from being destroyed in the acidic conditions. When the nano medicinal carrier was placed in a pH 7.4 condition (FIG. 3E), the nano medicinal carrier began to decompose to release the active agent (i.e., amoxicillin). These results show that the nano medicinal carrier of the present invention can avoid the destruction of gastric juice when entering into the acidic condition in the stomach, while when the nano medicinal carrier is attached on the gastric wall, it can release the active agent in the neutral condition (such as the condition in the gastric mucosa layer or the condition of gastric epithelial cells infected by *Helicobacter pylori*), and thereby, achieve the purpose of controlling medicine release.

Example 3

Testing of Pharmacological Effects (1) Colony Number Experiment

Small black mice were fed with a broth containing $1.0 \times 10^9$ CFU/ml *Helicobacter pylori* continually for 6 times in 2 weeks, to establish a *Helicobacter pylori*-infected animal model. The mice were fasted one night before fed with *Helicobacter pylori*, to decrease the mucus in the stomach, and thereby, increase the probability of infection. Then, the *Helicobacter pylori*-infected mice (6 mice each group) were fed with (a) the nano medicinal carrier obtained from example 1 (2) (control group); (b) 30 mg/kg amoxicillin; and (c) nano medicinal carrier (the concentration of amoxicillin, 30 mg/kg) obtained from example 1 (4) once daily for 10 days.

Then, the mice were sacrificed, and the tissue in the stomach was taken off to conduct the colony number experiment. The result is shown in Table 1.

TABLE 1

|  | control group | amoxicillin solution | solution of nano medicinal carrier encapsulating amoxicillin |
|---|---|---|---|
| The colony number of *Helicobacter pylori* in the stomach tissue of the mice | 502.3 ± 83.7 | 316.9 ± 30.5 | 63.2 ± 15.5 |

As shown in Table 1, as compared to the control group mice that were not treated by amoxicillin, the colony number of *Helicobacter pylori* in the stomach tissue of the mice fed with 30 mg/kg amoxicillin was decreased from 502.3±83.7 to 316.9±30.5, while the colony number of *Helicobacter* pylori in the stomach tissue of the mice fed with the nanocarrier encapsulating amoxicillin was further decreased to 63.2±15.5. These results show that the nano medicinal carrier of the present invention can effectively increase the treating effect of encapsulated active agent.

(2) *Campylobacter*-Like Organism Assay

Figure 4:
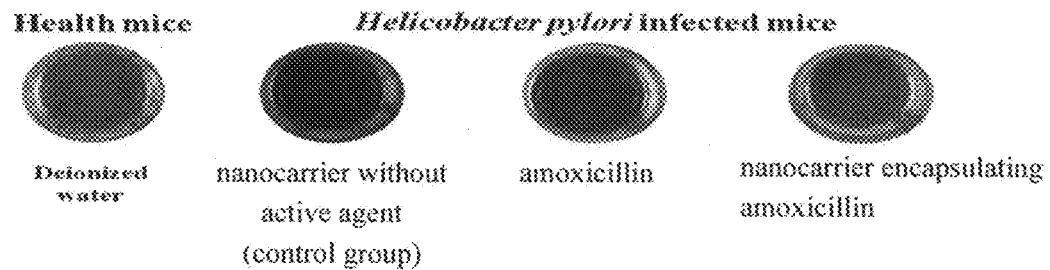
FIG. 4 is a picture showing the result of a *campylobacter*-like organism assay of mice.

*Campylobacter*-like organism assay (CLO assay) was conducted to evaluate the effect of nano medicinal carrier on treating the *Helicobacter pylori*-infected mice. The internal side of the stomach tissue of the *Helicobacter pylori*-infected mice was touch with CLO gel and compressed, the tissue was incubated at 37° C. for 12 hours, and the variation of the color of the CLO gel was observed. The results are shown in FIG. 4. The CLO gel without *Helicobacter pylori* (contacted with deionized water) is a yellow color. The CLO gel with a little of *Helicobacter pylori* is a yellow-orange color. The CLO gel with a lot of *Helicobacter pylori* is a red color. A darker color represents a higher amount of *Helicobacter pylori*.

As shown in FIG. 4, as compared to the stomach tissue of the mice fed with the nano medicinal carrier not encapsulating an active agent (control group; showing a dark red color) and the stomach tissue of the mice fed with amoxicillin (showing a red color), the amount of *Helicobacter pylori* in the stomach tissue of the mice fed with the nano medicinal carrier encapsulating amoxicillin (showing a yellow color) was significantly decreased. These results show that the nano medicinal carrier of the present invention can effectively increase the treating effect of an encapsulated active agent.

Example 4

Testing of Efficacy of the Nano Medicinal Carrier on Targeting *Helicobacter pylori*

(1) Step a: Preparation of a Fluorescent-Labeled Nano Medicinal Carrier Encapsulating a Fluorescent-Labeled Antibiotic Fluoresceinamine (FA; 0.0583 g) was dissolved in 1.0 ml acetonitrile to from a FA solution. Amoxicillin (0.1 g) was dissolved in 30 ml deionized water, and mixed with the aforesaid FA solution. 1-ethyl-3-(3-dimethylaminopropyl) carbodiimide (0.0408 g) was added thereto and magnetically stirred at room temperature in the dark for 12 hours to make FA to graft to the carboxyl group of amoxicillin to form a fluorescent-labeled FA-amoxicillin. And, finally, the sample was freeze-dried to collect the fluorescent-labeled FA-amoxicillin.

Then, a fucose-chitosan/heparin nano medicinal carrier crosslinked by genipin and encapsulating FA-amoxicillin was prepared according to the method described in example 1 (4), but amoxicillin was replaced by FA-amoxicillin. In addition, a fucose-chitosan/heparin nano medicinal carrier encapsulating FA-amoxicillin that was not cross-linked was prepared according to the method described in example 1 (4), but genipin was not added and amoxicillin was replaced by FA-amoxicillin. In addition, fucose-chitosan was labeled by Cy3 fluorescent dye to form a fluorescent-labeled Cy3-fucose-chitosan.

(2) Step B: Preparation of Fluorescent-Labeled *Helicobacter pylori*

To observe the cells infected by *Helicobacter* pylori, a DilC18(5)-DS molecular probe (excitation wavelength, 649 nm) was inserted in the cell membrane of *Helicobacter pylori* to form a fluorescent-labeled Dil-*Helicobacter pylori*. First, $1 \times 10^6$ *Helicobacter pylori* was mixed with 50 µl of a DilC18 (5)-DS molecular probe and 950 µl of a PBS buffer solution. The reaction was conducted under 30° C. water bath for 5 minutes, and then, under a 4° C. water bath for 15 minutes. The sample was centrifuged and the precipitate was collected to obtain the fluorescent-labeled Dil-*Helicobacter pylori*.

(3) Step C: Preparation of a Fluorescent-Labeled Dil-*Helicobacter pylori* Infected-Human Gastric Adenocarcinoma Cells A human gastric adenocarcinoma (AGS) cell line was incubated in a culture medium containing 10% FBS, and inoculated to transwell cell culture chambers (12 well/plate; 8 µm; growing area, 4.7 $cm^2$; MILLPORE). The cells were incubated for 24 to 30 days and then taken out. Next, the fluorescent-labeled Dil-*Helicobacter pylori* were co-cultured with the AGS cells for 2 hours to obtain a Dil-*Helicobacter pylori* infected AGS cell line.

(4) Step D: Targeting Assay

The FA-amoxicillin solution (100 µl) prepared from the above step A, targeting fluorescent-labeled nano medicinal carrier encapsulating FA-amoxicillin that was not cross-linked, and targeting fluorescent-labeled nano medicinal carrier crosslinked by genipin and encapsulating FA-amoxicillin were separately added and co-cultured with the Dil-*Helicobacter pylori*-infected AGS cell line. After 120 minutes, the targeting fluorescent-labeled nano medicinal carrier encapsulating a fluorescent labeled-antibiotic was observed by using a laser scanning confocal microscope to scan the fluorescent image to observe the targeting action on the cells infected by *Helicobacter pylori*. The FA-amoxicillin was used as a control group. The experimental results are shown in FIGS. 5A to 5C.

Figure 5A:
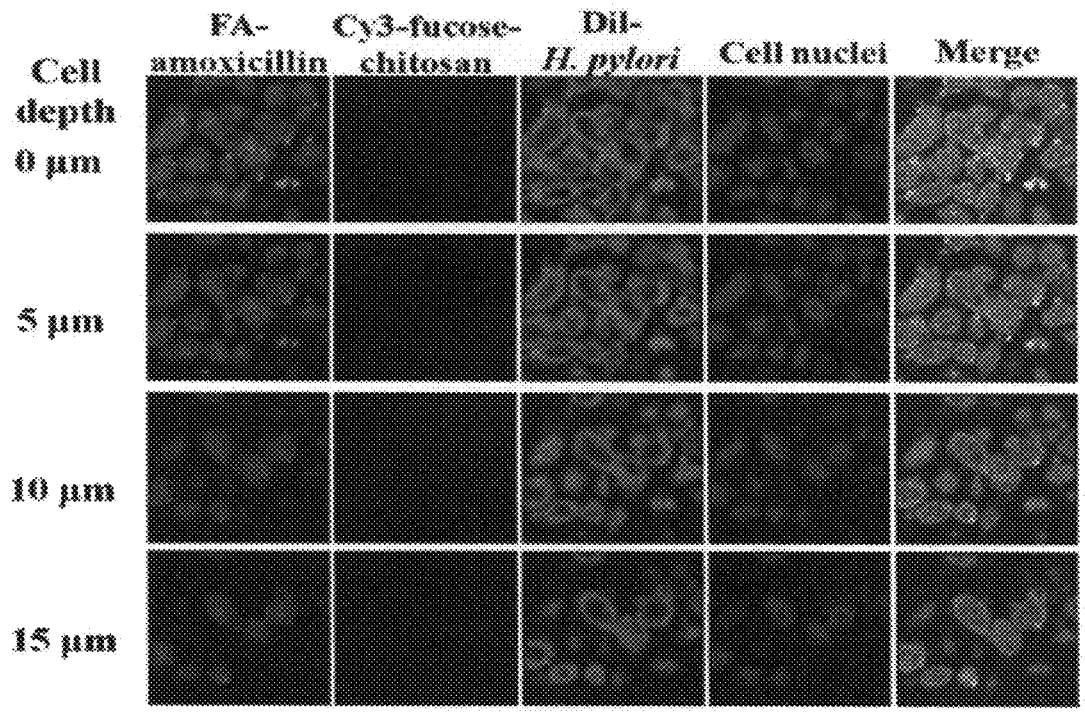
FIG. 5A is a fluorescent staining image showing the targeting of FA-amoxicillin solution to *Helicobacter pylori*.
Figure 5B:
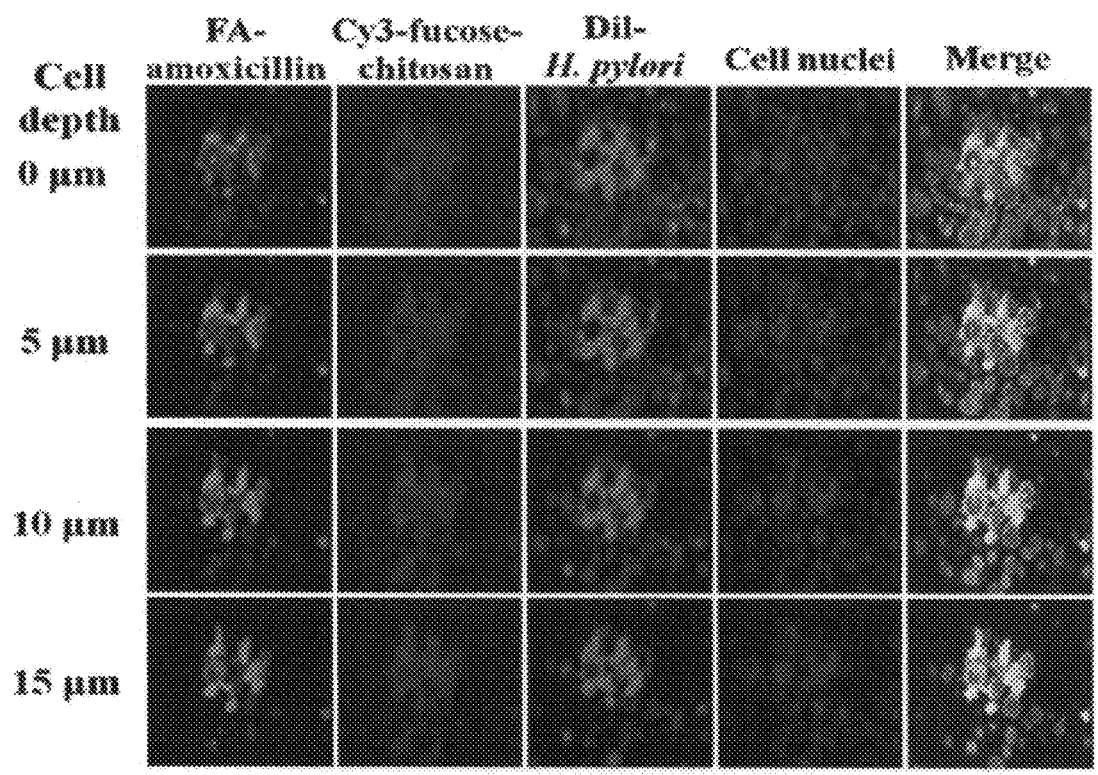
FIGS. 5B to 5C are fluorescent staining images showing the targeting of the nano medicinal carrier of the present invention to *Helicobacter pylori*.
Figure 5C:
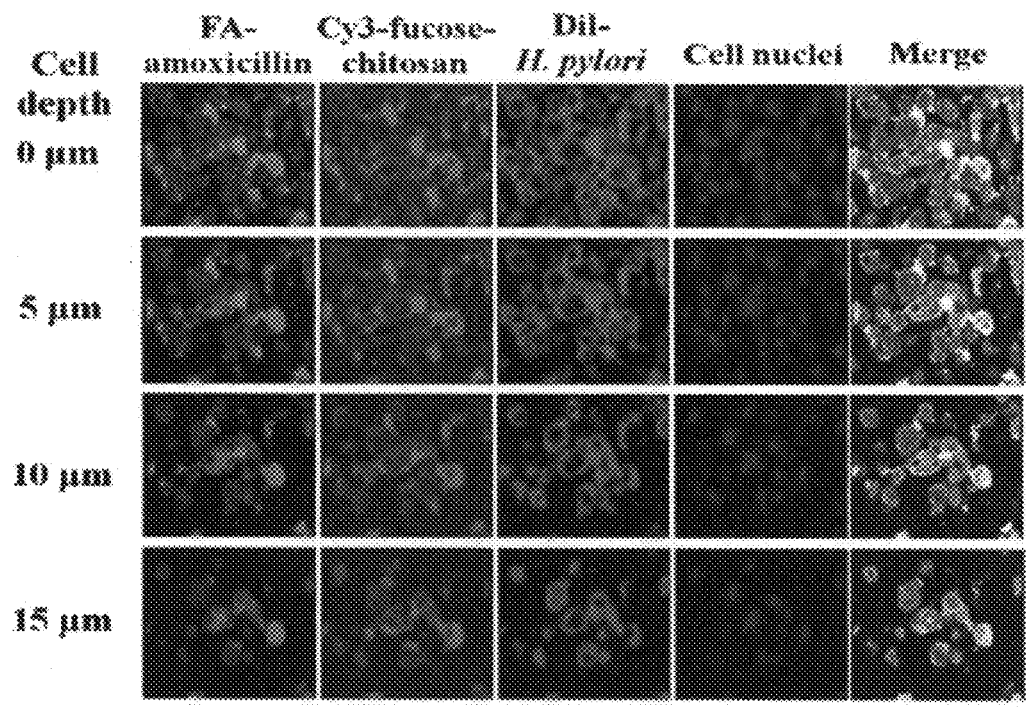

As shown in FIGS. 5A to 5C, when FA-amoxicillin solution was co-cultured with *Helicobacter pylori*-infected AGS cells, it is apparent that FA-amoxicillin did not enter into the AGS cells (FIG. 5A). When the targeting fluorescent-labeled nano medicinal carrier encapsulating FA-amoxicillin that was not cross-linked (FIG. 5B) or the targeting fluorescent-labeled nano medicinal carrier crosslinked by genipin and encapsulating FA-amoxicillin (FIG. 5C) was co-cultured with *Helicobacter pylori*-infected AGS cells, it is clear that the fluorescence of the FA-amoxicillin and Cy3-fucose-chitosan is observed in the cells (white spots in FIGS. 5B and 5C). These experimental results show that the medicinal carrier of the present invention indeed can bind with the surface of *Helicobacter pylori*. That is, the medicinal carrier of the present invention can target *Helicobacter pylori*, thereby increasing the anti-*Helicobacter pylori* efficacy of the encapsulated medicine.

The above examples are merely exemplified to illustrate the principle and efficacy of the present invention, but are not intended to limit the present invention. It is obvious to those skilled in the art that the various changes and modifications can be made in the technical spirit of the present invention, and thus, it is apparent that these changes and modifications are included within the scope of the appended claims and their equivalents.

What is claimed is:

1. A medicinal carrier, comprising:
   a first component, which is a biocompatible polymer with an amino group (—$NH_2$);
   a saccharide, which is selected from the group consisting of glucose, fucose, galactosamine, mannose, and combinations thereof; and
   a second component, which is a biocompatible material;
   wherein the saccharide grafts to the first component via the amino group (—$NH_2$) of the first component and the first component bonds to the second component via ionic bonding; and
   wherein the first component is selected from the group consisting of chitosan, collagen, gelatin, ethylene glycol-chitosan, poly(ethylene glycol)-chitosan, and combinations thereof; and the second component is selected from the group consisting of heparin, poly(glutamic acid), tripolyphosphoric acid, poly(acrylic acid), phospholipid, sodium alginate, tea polyphenol, and combinations thereof.

2. The carrier as claimed in claim 1, wherein the first component is selected from the group consisting of chitosan, gelatin, and combinations thereof; the second component is selected from the group consisting of heparin, poly(glutamic acid), sodium alginate, catechin, and combinations thereof; and the saccharide is fucose.

3. The carrier as claimed in claim 2, wherein the catechin comprises epigallocatechin gallate (EGCG).

4. The carrier as claimed in claim 1, further comprising a third component selected from the group consisting of an active agent, a protective agent, a crosslinking agent, and combinations thereof.

5. The carrier as claimed in claim 4, wherein the active agent is selected from the group consisting of amoxicillin, clarithromycin, tetracycline, metronidazole, curcumin, berberine, and combinations thereof; the protective agent is selected from the group consisting of trehalose, glucose, lactose, glycerol, and combinations thereof; and the crosslinking agent is selected from the group consisting of glutaraldehyde, genipin, epoxy resin, paraformaldehyde, formaldehyde, calcium chloride, and combinations thereof.

6. The carrier as claimed in claim 5, wherein the active agent is selected from the group consisting of amoxicillin, curcumin, and a combination thereof; the protective agent is trehalose; and the crosslinking agent is selected from the group consisting of genipin, calcium chloride, and combinations thereof.

7. The carrier as claimed in claim 6, which is a fucose-grafted chitosan/heparin nanocarrier encapsulating amoxicillin, a fucose-grafted chitosan/poly(glutamic acid) nanocarrier encapsulating curcumin, or a fucose-grafted chitosan/gelatin/EGCG nanocarrier.

8. The carrier as claimed in claim 7, which is a fucose-grafted chitosan/heparin nanocarrier crosslinked by genipin, encapsulating amoxicillin, and containing trehalose.

9. The carrier as claimed in claim 1, having a particle size of about 100 nm to about 4 µm.

10. The carrier as claimed in claim 9, having a particle size of about 150 nm to about 1 µm.

11. The carrier as claimed in claim 10, having a particle size of about 200 nm to about 500 nm.

12. A method for treating or alleviating a disease or condition associated with *Helicobacter pylori*, comprising administering to a subject in need an effective amount of the medicinal carrier as claimed in claim 1.

13. A method as claimed in claim 12, wherein the medical carrier is a fucose-grafted chitosan/heparin nanocarrier encapsulating amoxicillin, a fucose-grafted chitosan/poly(glutamic acid) nanocarrier encapsulating curcumin, or a fucose-grafted chitosan/gelatin/EGCG nanocarrier.

14. The method as claimed in claim 13, which is used for treating or alleviating peptic ulcer, gastritis or gastric cancer.

15. A method for preparing the medicinal carrier as claimed in claim 1, comprising:
   (a) providing a saccharide-grafted first component, wherein the first component is a biocompatible polymer with an amino group (—$NH_2$), and the saccharide is selected from the group consisting of glucose, fucose, galactosamine, mannose, and combinations thereof;
   (b) dissolving the saccharide-grafted first component into water to provide a first solution;
   (c) dissolving a second component into water to provide a second solution, wherein the second component is a biocompatible material;
   (d) optionally, providing a third solution comprising a third component selected from the group consisting of an active agent, a protective agent, a crosslinking agent, and combinations thereof; and
   (e) mixing the first solution, the second solution, and the optional third solution to form the medicinal carrier;
   wherein the first component is selected from the group consisting of chitosan, collagen, gelatin, ethylene glycol-chitosan, poly(ethylene glycol)-chitosan, and combinations thereof; and the second component is selected from the group consisting of heparin, poly(glutamic acid), tripolyphosphoric acid, poly(acrylic acid), phospholipid, sodium alginate, tea polyphenol, and combinations thereof.

16. The method as claimed in claim 15, wherein the step (e) comprises mixing the first solution and the second solution firstly, and then mixing with the third solution if present.

17. The method as claimed in claim 15, wherein the step (d) is present, and the step (e) of mixing the first solution, the second solution, and the third solution comprises:
   (e1) mixing the first solution and the third solution to form a first mixed solution;
   (e2) mixing the first mixed solution and an oily solution containing a surfactant to form a second mixed solution; and
   (e3) mixing the second mixed solution and the second solution to form the medicinal carrier.

18. The method as claimed in claim 15, wherein the first component and the second component are used in a weight ratio of about 1:0.1 to 1.

19. The method as claimed in claim 15, wherein the step (d) is present and the third component comprises the active agent, the protective agent, and the crosslinking agent, and the first component, the second component, the active agent, the protective agent, and the crosslinking agent are used in a weight ratio of about 1:0.1 to 1:0.1 to 1:1 to 10:0.02 to 0.2.

* * * * *